(12) United States Patent
Wadsworth et al.

(10) Patent No.: US 12,280,178 B2
(45) Date of Patent: *Apr. 22, 2025

(54) BIOPRINTED MENISCUS IMPLANT AND METHODS OF USING SAME

(71) Applicant: ASPECT BIOSYSTEMS LTD., Vancouver (CA)

(72) Inventors: Sam Wadsworth, Vancouver (CA); Simon Beyer, Richmond (CA); Tamer Mohamed, Richmond (CA); Konrad Walus, Vancouver (CA)

(73) Assignee: ASPECT BIOSYSTEMS LTD., Vancouver (CA)

( * ) Notice: Subject to any disclaimer, the term of this patent is extended or adjusted under 35 U.S.C. 154(b) by 0 days.

This patent is subject to a terminal disclaimer.

(21) Appl. No.: 18/241,754

(22) Filed: Sep. 1, 2023

(65) Prior Publication Data

US 2024/0173459 A1 May 30, 2024

Related U.S. Application Data

(63) Continuation of application No. 16/310,341, filed as application No. PCT/CA2017/050744 on Jun. 16, 2017, now Pat. No. 11,744,919.

(60) Provisional application No. 62/351,222, filed on Jun. 16, 2016.

(51) Int. Cl.
| | |
|---|---|
| *A61L 27/36* | (2006.01) |
| *A61F 2/30* | (2006.01) |
| *A61L 27/24* | (2006.01) |
| *A61L 27/38* | (2006.01) |
| *A61L 27/54* | (2006.01) |

(Continued)

(52) U.S. Cl.
CPC ............ *A61L 27/3654* (2013.01); *A61F 2/30* (2013.01); *A61L 27/24* (2013.01); *A61L 27/3817* (2013.01); *A61L 27/3834* (2013.01); *A61L 27/54* (2013.01); *B33Y 70/00* (2014.12); *B33Y 80/00* (2014.12); *A61F 2002/30985* (2013.01); *A61L 2300/41* (2013.01); *A61L 2300/414* (2013.01); *A61L 2430/06* (2013.01)

(58) Field of Classification Search
CPC .. A61L 27/3654; A61L 27/24; A61L 27/3817; A61L 27/3834; A61L 27/54; A61L 2430/06; A61F 2/30; A61F 2002/30985
See application file for complete search history.

(56) References Cited

U.S. PATENT DOCUMENTS

| | | | |
|---|---|---|---|
| 11,744,919 B2 * | 9/2023 | Wadsworth | A61L 27/3654 623/14.12 |
| 2016/0136895 A1 * | 5/2016 | Beyer | B33Y 30/00 425/132 |

FOREIGN PATENT DOCUMENTS

| | | | |
|---|---|---|---|
| WO | WO-2014197999 A1 * | 12/2014 | B29C 64/106 |

OTHER PUBLICATIONS

Fithian et al., "Material Properties and Structure-Function Relationships in the Menisci", Clinical Orthopaedics and Related Research, Issue 252, pp. 19-31 (1990).

(Continued)

*Primary Examiner* — Bruce E Snow
(74) *Attorney, Agent, or Firm* — Todd Lorenz

(57) ABSTRACT

Provided herein are meniscus implant compositions, as well as methods for making and using the same. The subject meniscus implants find us in repairing and/or replacing damaged or diseased meniscal tissue in a mammalian subject.

25 Claims, 11 Drawing Sheets

(51) Int. Cl.
  *B33Y 70/00*  (2020.01)
  *B33Y 80/00*  (2015.01)

(56) References Cited

OTHER PUBLICATIONS

Giri et al., "Modified chitosan hydrogels as drug delivery and tissue engineering systems: present status and applications." Acta Pharmaceutica Sinica B., vol. 2(5), pp. 439-449 (2012).
Jun et al. "Microfluidic spinning of micro-and nano-scale fibers for tissue engineering", Lab on a Chip 14.13, pp. 2145-2160 (2014).
Makris et al., "The knee meniscus: structure-function, pathophysiology, currrent repari techniques, and prosepects for regeneration", Biomaterials, vol. 32(30), pp. 7411-7431 (2011).
Markstedt et al., "3D Bioprinting Human Chondrocytes with Nanocelluslose-Alginate Bioink for Cartilage Tissue Engineering Applications", Biomacromolecules, vol. 16, No. 5, pp. 1489-1496 (2015).

* cited by examiner

BIOPRINTED MENISCUS IMPLANT AND METHODS OF USING SAME

CROSS REFERENCE TO RELATED APPLICATIONS

This application is a continuation of U.S. patent application Ser. No. 16/310,341, filed Dec. 14, 2018, now U.S. Pat. No. 11,744,919, which is a National Stage Entry of PCT/CA2017/050744, filed Jun. 16, 2017, which claims priority benefit of the filing date of U.S. Provisional Patent Application Ser. No. 62/351,222, filed Jun. 16, 2016, the disclosure of each of which is herein incorporated by reference in its entirety.

FIELD OF THE INVENTION

The invention provides synthetic tissue structures and methods for their fabrication and use, including artificial meniscus implants, comprising precisely patterned layers containing a variable synthetic tissue fiber structure dispensed from a bioprinter.

BACKGROUND OF THE INVENTION

The meniscus is one of the most commonly damaged areas of the knee joint, with a mean incidence of injury in the United States of 66 injuries per 100,000 people. Complete or partial removal of the meniscus relieves acute pain, but without adequate replacement, meniscus removal can lead to damage of the articular cartilage of the knee, leading to osteoarthritis (OA). The meniscus typically demonstrates poor healing potential, and none of the currently available meniscal replacement options meets the necessary load-bearing and biomechanical requirements of this unique tissue, while also successfully engrafting into the surrounding tissue to provide a long-term solution to meniscus injury.

The tissue engineering art has long sought to fabricate viable synthetic structures capable of mimicking and/or replacing living organs and tissues using myriad materials and methods. Historically, cells and other biological materials were seeded into pre-formed three-dimensional scaffolds imparting a desired structure, with the scaffold preferably being biodegradable or otherwise removable. See, e.g. U.S. Pat. No. 6,773,713. Despite decades of development, however, significant challenges remain with this approach in respect of effective cell seeding and growth, and the technique does not work for more complex physiological structures involving more complicated spatial arrangements of different cell types.

More recently, 3D printing, a form of additive manufacturing (AM), has been applied to create three-dimensional objects directly from digital files, wherein the object is built up layer-by-layer to achieve the desired three dimensional structure. Initial efforts to adapt 3D printing techniques to the creation of cellular constructs and tissues, termed 3D bioprinting, also focused on initial printing of scaffold materials independent of the direct seeding or subsequent printing of the cellular materials, consistent with the above convention. See, e.g. U.S. Pat. Nos. 6,139,574; 7,051,654; 8,691,274; 9,005,972 and 9,301,925. Unfortunately, however, the polymers typically employed to form the prior art scaffolds, while generally considered biocompatible, are not physiologically compatible. As such, cell viability is sacrificed with this approach in favor of the mechanical stability of the requisite scaffold.

In the meniscus implant art in particular, for example, Bakarich et al. described a system in which a combination of an alginate/acrylamide gel precursor solution and an expoxy based UV-curable adhesive were combined to form a printable matrix material. *ACS Appl. Mater. Interfaces* 6:15998-16006 (2014). The printable matrix material was used in a 3D bioprinting process to deposit a 2D layer of the matrix material alone, after which UV light was passed over the layer for one to five minutes to solidify it before depositing another layer on top. Due to the non-physiologic nature of the acrylamide gel and epoxy-based UV-curable matrix components, however, living cells cannot be maintained in this matrix material during the bioprinting process, and the resulting scaffold is still non-conducive to cell growth, differentiation and communication.

Alternative 3D bioprinting techniques have also been described emphasizing the converse, wherein mechanical structure and printing fidelity are sacrificed in favor of cell viability. These bioprinting systems create synthetic tissues by depositing cellular materials within a biocompatible matrix, which is then cross-linked or otherwise solidified after deposition to create a solid or semi-solid tissue structure. See, e.g., U.S. Pat. Nos. 9,227,339; 9,149,952; 8,931,880 and 9,315,043; U.S. Patent Publication Nos. 2012/0089238; 2013/0345794; 2013/0164339 and 2014/0287960. With all of these systems, however, the temporal delay between the deposition and crosslinking steps invariably leads to a lack of control over the geometry of the printed structure, as well as the cellular and matrix composition of the structure. Moreover, cellular viability is often still compromised in any event by the subsequent cross-linking or solidification event.

As but one example of this problem, Markstedt et al. described a system in which hydrogels, such as collagen, hyaluronic acid, chitosan and alginate were used in combination with non-physiologic reinforcing fiber materials, such as nanofibrillated cellulose, as a bio-ink for 3D bioprinting. *BioMacromolecules* 16:1489-96 (2015). This bio-ink is deposited as a 2D layer of material, which is submerged in a divalent cation bath ($CaCl_2$)) to crosslink for ten minutes and solidify the first layer before depositing another layer on top. Although living cells were successfully incorporated into their bio-ink, a cell viability analysis demonstrated that the cell viability decreased significantly as a result of the cross-linking process, from ~95.3% before embedding, to ~69.9% after embedding and crosslinking. Furthermore, a comparison to non-printed controls revealed that the decrease in cell viability was likely due to the preparation and mixing of the bio-ink itself, rather than the actual 3D printing process.

Accordingly, existing 3D bioprinting techniques and materials have failed to satisfactorily resolve the technical conflict between structural integrity and printing fidelity on the one hand, and physiological compatibility and cellular viability on the other. The current invention addresses these and other unmet needs. All prior art references listed herein are incorporated by reference in their entirety.

SUMMARY OF INVENTION

The present invention successfully resolves the previously conflicting objectives in the 3D bioprinting art between structural integrity and cellular viability, providing synthetic tissue structures deposited in solidified form with improved cell growth and/or survival characteristics and physiological functionality, and without the need for cross-linking or other subsequent solidification steps. Aspects of the present invention include synthetic tissue structures comprising one or more layers deposited by a bioprinter, wherein each layer comprises synthetic tissue fiber(s) comprising a solidified biocompatible matrix optionally comprising cells, and optionally comprising one or more active agents, wherein at least one of the matrix material, cell type, cell density, and/or amount of an active agent varies in at least one direction within the layers. Preferably, at least one of said layers comprises a single continuous synthetic tissue fiber dispensed from the bioprinter having a variable composition.

In specific embodiments, meniscus implants are provided comprising layers of synthetic tissue fiber(s) dispensed from a bioprinter as a solidified biocompatible matrix optionally comprising cells, and optionally comprising one or more active agents, wherein at least one of the matrix material, cell type, cell density, and/or amount of an active agent varies in at least one direction within the layers. Preferably, at least one of said layers comprises a continuous synthetic tissue fiber dispensed from the bioprinter having a variable composition. More preferably, each of said layers comprises a continuous synthetic tissue fiber having a variable composition. Still more preferably, a meniscus implant comprises a reinforced peripheral region, and/or at least one anchor region, as described herein.

In one aspect, the invention provides a synthetic tissue structure comprising a plurality of layers deposited by a bioprinter, each layer comprising synthetic tissue fiber(s) comprising a solidified biocompatible matrix optionally comprising cells, and optionally comprising one or more active agents, wherein at least one of said layers comprises a matrix material varying in type and/or amount in at least one direction. In some embodiments, each layer comprises a matrix material varying in type and/or amount in at least one direction.

In another aspect, the invention provides a synthetic tissue structure comprising a plurality of layers, each layer comprising synthetic tissue fiber(s) comprising a plurality of mammalian cells dispensed from a bioprinter within a solidified biocompatible matrix, wherein at least one of said layers comprises a cell type and/or cell density varying in at least one direction. In some embodiments, each layer comprises a cell type and/or cell density varying in at least one direction.

In another aspect, the invention provides a synthetic tissue structure comprising a plurality of layers deposited by a bioprinter, each layer comprising synthetic tissue fiber(s) comprising a solidified biocompatible matrix optionally comprising cells, wherein at least one of said layers comprises an active agent varying in type and/or amount in at least one direction. In some embodiments, each layer comprises an active agent varying in type and/or amount in at least one direction.

In some embodiments, one or more synthetic tissue fibers are dispensed in a desired pattern or configuration to form a first layer, and one or more additional layers are then dispensed on top, having the same or a different pattern or configuration. In certain embodiments, a plurality of layers are stacked to form a three dimensional structure that can be used as an artificial meniscus implant. Preferably, at least one of said layers comprises a single continuous synthetic tissue fiber dispensed from the bioprinter having a variable composition. More preferably, each of said layers comprises a single continuous synthetic tissue fiber having a variable composition.

In some embodiments, a synthetic tissue structure comprises a number of individual layers that ranges from about 1 to about 250, such as about 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 200, 205, 210, 215, 220, 225, 230, 235, 240 or about 245 individual layers. Any suitable number of individual layers can be incorporated to generate a tissue structure having desired dimensions.

In some embodiments, one or more individual fibers and/or layers are organized to create one or more zones within a tissue structure, wherein each zone has one or more desired properties (e.g., one or more mechanical and/or biological properties). As used herein, the term "region" refers to a portion of a tissue structure defined in an x-y plane (e.g., an area or portion of an individual layer, where each layer of the tissue structure defines an x-y plane), whereas the term "zone" refers to a portion of a tissue structure defined in the z-direction and comprising at least two contiguous regions from separate x-y planes, or layers (e.g., a "macrolayer" that comprises a plurality of individual "microlayers").

Zones in accordance with embodiments of the invention can have any desired three dimensional geometry, and can occupy any desired portion of a synthetic tissue structure. For example, in some embodiments, a zone can span an entire length, width, or height of a synthetic tissue structure. In some embodiments, a zone spans only a portion of a length, width, or height of a synthetic tissue structure. In some embodiments, a synthetic tissue structure comprises a plurality of different zones that are organized along a length, width, height, or a combination thereof, of the synthetic tissue structure. In one preferred embodiment, a synthetic tissue structure comprises three different zones that are organized along the height of the synthetic tissue structure, such that a path through the synthetic tissue structure from the bottom to the top would pass through all three zones.

In some embodiments, a zone can comprise a number of layers that ranges from about 2 to about 250, such as about 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 200, 205, 210, 215, 220, 225, 230, 235, 240 or about 245 individual layers. In some embodiments, the individual layers within a zone are organized in a manner that confers one or more mechanical and/or biological properties on the zone. For example, in some embodiments, the individual layers within a zone comprise one or more reinforcing materials that confer increased mechanical strength on the zone. In some embodiments, the individual layers within a zone comprise one or more materials that confer desirable cell growth properties on the zone. In some embodiments, the individual layers within a zone, or the plurality of individual compartments of a fiber structure passing through the zone, can be alternated in a manner that confers desirable properties on the zone. For example, in some embodiments, the individual layers or regions within a zone are alternated such that the odd numbered layers contain one or more reinforcing materials that confer desirable mechanical properties on the zone, and the even numbered layers contain one or more materials that confer desirable biological properties on the zone (e.g., softer materials that are conducive to cell migration, growth, viability, and the like). In some embodiments, a zone comprises a plurality of contiguous individual layers (e.g., about 2, 3, 4, 5, 6, 7, 8, 9 or about 10 or more contiguous layers) that comprise one or more reinforcing materials that confer increased mechanical strength on the zone, which contiguous layers are alternated with another plurality of contiguous individual layers (e.g., about 2, 3, 4, 5, 6, 7, 8, 9 or about 10 or more contiguous layers) that comprise one or more materials that confer desirable biological properties on the zone (e.g., softer materials that are conducive to cell migration, growth, viability, and the like).

In one aspect, an artificial meniscus implant comprises at least one basal zone, at least one interior zone, and at least one superficial zone, wherein at least one of said zones comprises a layer comprising a synthetic tissue fiber(s) comprising a solidified biocompatible matrix, wherein the matrix materials vary in type and/or amount between the center of a layer and the periphery of the layer. In some embodiments, one or more matrix materials at or near the periphery of the layer comprise a reinforced matrix material.

Aspects of the invention also include artificial meniscus implants that comprise one or more anchor regions. As used herein, the term "anchor region" refers to a region that comprises one or more reinforced matrix materials. Artificial meniscus implants in accordance with embodiments of the invention can include any suitable number of anchor regions, such as 1 to 12, such as 2, 3, 4, 5, 6, 7, 8, 9, 10 or 11 anchor regions. In some embodiments, an artificial meniscus implant comprises no anchor regions.

In another aspect, artificial meniscus implants are provided comprising at least one basal zone, at least one interior zone, and at least one superficial zone, wherein at least one zone comprises a layer comprising at least one synthetic tissue fiber comprising a plurality of mammalian cells dispensed from a bioprinter within a solidified biocompatible matrix, wherein at least one layer comprises a cell density that varies in at least one direction. In some embodiments, each of said layers comprises a cell density that varies in at least one direction. In some embodiments, the cell density ranges from 0 to about 100×10$^6$ cells/mL.

In another aspect, artificial meniscus implants in accordance with embodiments of the invention include at least one basal zone, at least one interior zone, and at least one superficial zone, wherein at least one layer in one of said zones comprises a synthetic tissue fiber(s) comprising a solidified biocompatible matrix and at least one active agent, wherein the at least one active agent varies in type and/or amount between the center of the layer and the periphery of the layer.

In some embodiments, the biocompatible matrix on the periphery of the layer may comprise at least one active soluble agent that is released over time from the matrix to encourage host vascular cell ingrowth and chondrocyte cell ingrowth. Such bioactive agents include, but are not limited to: vascular endothelial growth factor (VEGF), fibroblast growth factor (FGF), insulin-like growth factor-1 (IGF-1), bone morphogenetic factors. hepatocyte scatter factor, urokinase plaminogen activator, transforming growth factor-β (TGF-β), platelet derived growth factor (PDGF), or any combination thereof.

In some embodiments, the biocompatible matrix on the periphery of the layer may comprise at least one insoluble factor to encourage cell ingrowth. Non-limiting examples of such insoluble factors include: hyaluronic acid or sulfated hyaluronic acid, fibronectin, fibrin, and collagen I. Additional bioactive factors can be incorporated into the matrix arranged in the interior of the subject artificial meniscus implants to encourage collagen deposition by chondrocytes including. Non-limiting examples of such additional bioactive factors include: insulin, connective tissue-derived growth factor (CTGF), or a combination thereof.

In some embodiments, portions or regions of the periphery will comprise at least one active agent. In some embodiments, the entire periphery of a layer comprises at least one active agent. In some embodiments, the periphery comprises a plurality of active agents. In some embodiments the entire periphery of the layer includes an active agent that reduces the host inflammatory response, for example, via the inclusion of one or more steroid compounds contained within one of more microparticles to ensure sustained release over an extended time period.

In some embodiments, an artificial meniscus implant has an arcuate shape that has an anterior end, a posterior end, a middle section therebetween defining a curved path between said anterior and posterior ends, an internal side, and an external side. In some embodiments, the cell density increases in a radial manner from the internal side towards the external side. In some embodiments, the concentration of reinforced matrix materials increases in a radial manner from the internal side towards the external side. In some embodiments, the amount of active agent increases in a radial manner from the internal side towards the external side.

In some embodiments, the basal zone comprises one or more layers comprising randomly-oriented synthetic tissue fiber(s); the interior zone comprises one or more layers comprising circumferentially-oriented synthetic tissue fiber(s) and radially-oriented synthetic tissue fiber(s); and the superficial zone comprises one or more layers comprising randomly-oriented synthetic tissue fiber(s). In some embodiments, the circumferentially-oriented synthetic tissue fiber(s) has a first diameter and the radially-oriented synthetic tissue fiber(s) has a second, different diameter. In some embodiments, the circumferentially-oriented synthetic tissue fiber(s) and the radially-oriented synthetic tissue fiber(s) have the same diameter. In some embodiments, the synthetic tissue fiber(s) has a diameter that ranges from about 20 μm to about 500 μm.

In some embodiments, the circumferentially-oriented synthetic tissue fiber(s) comprises a first solidified biocompatible matrix, and the radially-oriented synthetic tissue fiber(s) comprises a second, different solidified biocompatible matrix. In some embodiments, the circumferentially-oriented synthetic tissue fiber(s) and the radially-oriented synthetic tissue fiber(s) comprise the same solidified biocompatible matrix.

In some embodiments, the interior zone comprises a layer comprising a synthetic tissue fiber(s) that is configured to promote deposition of collagen fibers aligned with a longitudinal direction of the synthetic tissue fiber(s). In some embodiments, the interior zone comprises a layer comprising a circumferentially-oriented synthetic tissue fiber(s) that is configured to promote deposition of collagen fibers that are aligned with a longitudinal direction of the circumferentially-oriented synthetic tissue fiber(s). In some embodiments, the interior zone comprises a layer comprising a radially-oriented synthetic tissue fiber(s) that is configured to promote deposition of collagen fibers that are aligned with a longitudinal direction of the radially-oriented synthetic tissue fiber(s).

The solidified biocompatible matrix can comprise any of a wide variety of natural or synthetic polymers that support the viability of living cells, including, e.g., alginate, laminin, fibrin, hyaluronic acid, poly(ethylene) glycol based gels, gelatin, chitosan, agarose, or combinations thereof. In preferred embodiments, the solidified biocompatible matrix comprises alginate, or other suitable biocompatible polymers that can be instantaneously solidified while dispensing from the print head. In further preferred embodiments, the solidified biocompatible matrix comprises a homogeneous composition of alginate throughout the radial cross section of each synthetic tissue fiber.

In particularly preferred embodiments, the solidified biocompatible matrix is physiologically compatible, i.e., conducive to cell growth, differentiation and communication. In some such embodiments, the physiologically compatible matrix comprises alginate in combination with one or more of: collagen, fibronectin, thrombospondin, glycosaminoglycans (GAG), deoxyribonucleic acid (DNA), adhesion glycoproteins, elastin, and combinations thereof. In specific embodiments, the collagen is selected from the group consisting of: collagen I, collagen II, collagen III, collagen IV, collagen V, collagen VI, or collagen XVIII. In specific embodiments, the GAG is selected from the group consisting of: hyaluronic acid, chondroitin-6-sulfate, dermatan sulfate, chondroitin-4-sulfate, or keratin sulfate.

As reviewed above, anchor regions can be generated by the incorporation of higher strength materials into specific zones of an implant (i.e., suture points), for example, stiffer synthetic materials, including, but not limited to, polycaprolactone (PCL), poly(lactic-co-glycolic acid) (PLGA), polyurethane (PU) and any combination thereof. In some embodiments, an anchor region can contain double network hydrogels, generated by combining at least two different hydrogel materials, examples of which include, without limitation, alginate, Gelatin methacrylol (GelMA), methacryloyl polyethylene glycol (PEGMA), gellan gum, agarose, polyacrylamide, or any combination thereof. In addition, high strength fibers can be generated from high concentrations of biological polymers including, without limitation, collagen, chitosan, silk fibroin, or any combination thereof, and these biological polymers can be incorporated into one or more anchor regions. In some embodiments, an anchor region and/or a reinforced peripheral region of an implant comprises one or more layers of high strength material(s) deposited in alternation in the z-direction with one or more layers of softer matrix materials containing, e.g., hydrogel material(s) conducive to cell survival and ingrowth described above. In this way, the softer, cell compatible hydrogel materials provide one or more desirable biological functions, and the stiffer materials provide one or more desirable mechanical functions, to generate a hybrid structure with appropriate mechanical and biological functions.

In some embodiments, the mammalian cells are selected from the group consisting of: fibroblasts, chondrocytes, fibrochondrocytes, primary human meniscus-derived chondrocytes, stem cells, bone marrow cells, embryonic stem cells, mesenchymal stem cells, bone marrow-derived mesenchymal stem cells, induced pluripotent stem cells, differentiated stem cells, tissue-derived cells, microvascular endothelial cells, and combinations thereof. In preferred embodiments, the cell viability within the synthetic living tissue structures ranges from about 70% up to about 100%, such as about 75%, about 80%, about 85%, about 90%, about 95%, about 98%, about 99%, about 99.5%, or about 99.9% in comparison with cell viability before printing.

In some embodiments, the meniscus implant further comprises an acellular sheath positioned below the basal zone. In some embodiments, the meniscus implant further comprises an acellular sheath positioned above the superficial zone. In some embodiments, the meniscus implant comprises a first acellular sheath positioned below the basal zone and a second acellular sheath positioned about the superficial zone.

In some embodiments, the meniscus implant further comprises at least one active agent. In some embodiments, the at least one active agent is selected from the group consisting of: TGF-β1, TGF-β2, TGF-β3, BMP-2, BMP-4, BMP-6, BMP-12, BMP-13, basic fibroblast growth factor, fibroblast growth factor-1, fibroblast growth factor-2, platelet-derived growth factor-AA, platelet-derived growth factor-BB, platelet rich plasma, IGF-I, IGF-II, GDF-5, GDF-6, GDF-8, GDF-10, vascular endothelial cell-derived growth factor, pleiotrophin, endothelin, nicotinamide, glucagon like peptide-I, glucagon like peptide-II, parathyroid hormone, tenascin-C, tropoelastin, thrombin-derived peptides, laminin, biological peptides containing cell-binding domains and biological peptides containing heparin-binding domains, therapeutic agents, and any combinations thereof.

In preferred embodiments, the bioprinter dispenses the solidified biocompatible matrix comprising the plurality of mammalian cells through a single orifice. In particularly preferred embodiments, the single orifice is comprised within a print head such as that described and claimed in WO 2014/197999, the disclosure of which is herein incorporated by reference in its entirety.

DETAILED DESCRIPTION

Aspects of the present invention include synthetic tissue structures comprising one or more layers deposited by a bioprinter, wherein each layer comprises synthetic tissue fiber(s) comprising a solidified biocompatible matrix optionally comprising cells, and optionally comprising one or more active agents, wherein at least one of the matrix material, cell type, cell density, and/or amount of an active agent varies in at least one direction within the layers. Preferably, at least one of said layers comprises a single continuous synthetic tissue fiber dispensed from the bioprinter having a variable composition. The term "solidified" as used herein refers to a solid or semi-solid state of material that maintains its shape fidelity and structural integrity upon deposition. The term "shape fidelity" as used herein means the ability of a material to maintain its three dimensional shape. In some embodiments, a solidified material is one having the ability to maintain its three dimensional shape for a period of time of about 30 seconds or more, such as about 1, 10 or 30 minutes or more, such as about 1, 10, 24, or 48 hours or more. The term "structural integrity" as used herein means the ability of a material to hold together under a load, including its own weight, while resisting breakage or bending.

In some embodiments, a solidified composition is one having an elastic modulus greater than about 15, 20 or 25 kilopascals (kPa), more preferably greater than about 30, 40, 50, 60, 70, 80 or 90 kPa, still more preferably greater than about 100, 110, 120 or 130 kPa. Preferred elastic modulus ranges include from about 15, 25 or 50 Pa to about 80, 100, 120 or 140 kPa.

Additional aspects of the invention include artificial meniscus implants for use in repairing and/or replacing a damaged or diseased meniscal tissue in a mammalian subject, comprising synthetic tissue fiber(s) dispensed from a bioprinter as a solidified biocompatible matrix optionally containing cells, and optionally containing one or more active agents, wherein at least one of the matrix material, cell type, cell density, and/or type and/or amount of an active agent varies in at least one direction within the fiber.

Figure 1:
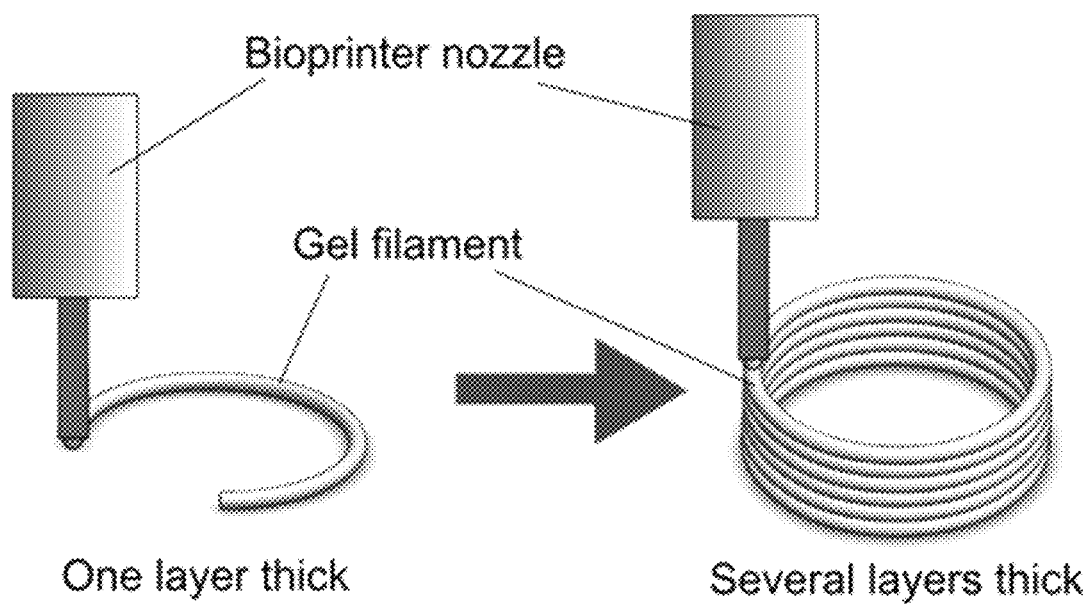
FIG. 1 is a schematic depiction of a layer-by-layer synthetic tissue fiber deposition process.

As provided in FIG. 1, a solidified biocompatible matrix optionally containing a plurality of mammalian cells is dispensed from a bioprinter forming one or more synthetic tissue fiber(s) on a deposition surface, and ultimately forming a layer. As such, subsequent cross-linking or other solidification steps are unnecessary after dispensation of the already-solidified matrix from the printhead. Accordingly, a second layer can be rapidly deposited on top of the first layer, while maintaining the structural integrity of the first layer, and this process can be continued to deposit a plurality of layers, one on top of the next, until a three dimensional structure having a desired geometry is obtained.

The solidified biocompatible matrix may advantageously comprise alginate, or any other suitable biocompatible polymer that can be instantaneously solidified while dispensing from the printhead. In a preferred embodiment, the alginate-based matrix is printed and simultaneously crosslinked at the time of printing by contacting with a divalent cation cross-linking solution (e.g., a $CaCl_2$) solution) before or upon dispensation from the printhead. In particularly preferred embodiments, the alginate-based biocompatible matrix further comprises one or more physiological materials, as described in more detail herein. In further preferred embodiments, the solidified biocompatible matrix comprises a homogeneous composition of alginate throughout the radial cross section of each synthetic tissue fiber.

In some embodiments, a synthetic tissue fiber structure comprises a plurality of individual compartments (organized along the length of the synthetic tissue fiber) that are created by sequentially depositing different matrix materials (e.g., natural and/or synthetic polymers), different cell types, different cell concentrations, and/or different types and/or amounts of active agents in each compartment of the same continuous synthetic tissue fiber structure. For example, in some embodiments, a synthetic tissue fiber structure comprises a first compartment that comprises a first matrix material, and a second compartment that comprises a second matrix material. In some embodiments, a synthetic tissue fiber structure comprises a first compartment that comprises a first cell type, and a second compartment that comprises a second cell type. In some embodiments, a synthetic tissue fiber structure comprises a first compartment that comprises a first cell concentration, and a second compartment that comprises a second cell concentration. In some embodiments, a synthetic tissue fiber structure comprises a first compartment that comprises a first active agent, and a second compartment that comprises a second active agent. Any combination of matrix materials, cell types, cell concentrations, and/or types and/or amounts of active agents can be used in different compartment of a subject synthetic tissue fiber structure to achieve desired biomechanical properties and/or biological activities.

Synthetic tissue fiber structures in accordance with embodiments of the invention can include controlled patterning of different matrix materials (e.g., natural and/or synthetic polymers) and crosslinking techniques to create a desired cross-sectional profile within a given compartment. For example, in some embodiments, a synthetic tissue fiber structure comprises a compartment having a solid, tubular, or porous cross-sectional profile. Non-limiting examples of cross-sectional profiles that can be created in a synthetic tissue fiber structure in accordance with embodiments of the invention include those described in Jun, Yesl, et al. "Microfluidic spinning of micro- and nano-scale fibers for tissue engineering." *Lab on a Chip* 14.13 (2014): 2145-2160, the disclosure of which is incorporated herein by reference in its entirety.

In some embodiments, the resulting synthetic tissue fiber is patterned, using software tools, to form layers optionally containing a plurality of mammalian cells and/or a plurality of biocompatible matrix materials. In certain embodiments, a plurality of layers is deposited in a sequential manner to generate a multi-layered meniscus implant comprising a plurality of zones. In some embodiments, a meniscus implant comprises at least one basal zone, at least one interior zone, and at least one superficial zone, wherein the interior zone comprises at least one layer comprising at least one circumferentially-oriented synthetic tissue fiber, and at least one radially-oriented synthetic tissue fiber. Preferably, at least one of said layers comprises a single continuous synthetic tissue fiber dispensed from the bioprinter having a variable composition.

One advantage of the subject meniscus implants is that the matrix composition, cell type, cell density, and active agent type and/or concentration can be controlled at any given point in any portion of any layer of the implant, thereby facilitating the generation of meniscus implants more closely resembling the natural architecture of a meniscus tissue, and that possess desirable biomechanical properties, including, but not limited to, reinforced anchor regions on the periphery of the implant, circumferentially- and radially-oriented fiber structures within the meniscus implant, as well as specific cell types and cell densities within specific regions and/or zones of the implant.

Another advantage of the present invention is that one or more active agents (described in more detail herein) can be selectively added to different compartments of a synthetic tissue fiber to allow precise localization of an active agent within one or more layers of a meniscus implant, including, but not limited to, increased concentrations of appropriate active agents on the periphery of an acellular implant to encourage the ingrowth of endogenous cells. The subject meniscus implants are described in further detail below.

Figure 2:
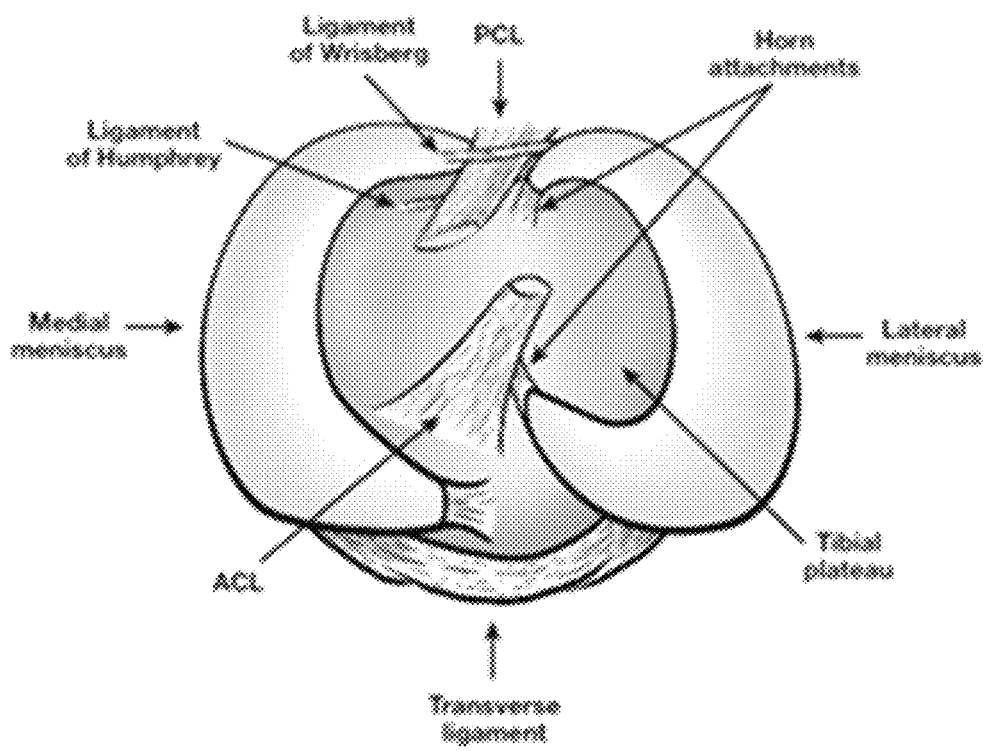
FIG. 2 is a schematic illustration of a knee joint, depicting a lateral and a medial meniscus. (Adapted from: The knee meniscus: structure-function, pathophysiology, current repair techniques, and prospects for regeneration. Biomaterials. 2011 October; 32(30): 7411-7431. doi:10.1016/j.biomaterials.2011.06.037, Eleftherios A. Makris, MD1, Pasha Hadidi, BS1, and Kyriacos A. Athanasiou, Ph.D., P.E.1).
Figure 3:
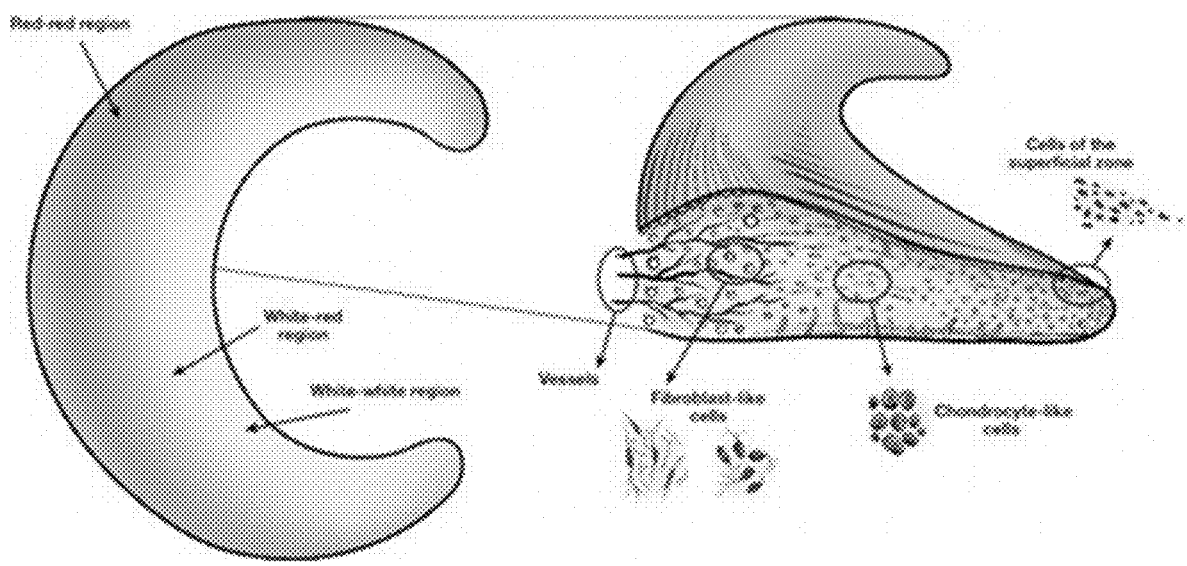
FIG. 3 is a schematic illustration of a meniscus, depicting both a top view and a cross sectional view. The outer (red-red) region, central (white-red) region, and the inner (white-white) region are depicted. (Adapted from: The knee meniscus: structure-function, pathophysiology, current repair techniques, and prospects for regeneration. Biomaterials. 2011 October; 32(30): 7411-7431. doi:10.1016/j.biomaterials.2011.06.037, Eleftherios A. Makris, MD1, Pasha Hadidi, BS1, and Kyriacos A. Athanasiou, Ph.D., P.E.1).

Meniscus Anatomy:

The menisci are a pair of crescent-shaped fibrocartilages comprised of both a medial and a lateral component situated between the corresponding femoral condyle and tibial plateau. (FIG. 2). The anterior and posterior insertional ligaments attach the menisci firmly, and they fix the meniscus to the tibial plateau well. Menisci are generally wedge-shaped, and the lateral menisci are approximately 32.4-35.7 mm in length, and approximately 26.6-29.3 mm wide, while the medial menisci are approximately 40.5-45.5 mm long and approximately 27 mm wide. Each is a glossy-white, complex tissue comprised of cells, specialized extracellular matrix (ECM) materials, and zone-specific innervation and vascularization. The menisci are fully vascularized at birth, however, over time the blood vessels retreat outwards until (in humans) at 10 years of age, approximately 10-30% of the meniscus at the periphery is vascularized. The adult human meniscus thus has two distinct zones, the outer, vascular/neural zone (red-red zone), and the inner completely avascular/aneural zone (white-white zone). These regions are separated by the narrow central (red-white) zone that contains features of both the outer (red-red) and the inner (white-white) zones (FIG. 3). Critically, the self-healing capacity of each area is directly related to blood supply, leaving the inner, white-white zone susceptible to trauma and degenerative lesions.

Meniscus Cellular and Biochemical Composition

The meniscus is a highly hydrated tissue comprising approximately 72% water, with the remaining 28% mostly comprising ECM and cells. Collagens make up most of the ECM (75%) followed by glycosaminoglycans (GAGs, 17%) DNA (2%), adhesion glycoproteins (<1%) and elastin (<1%). These ratios vary depending on the zone of the tissue, age, and condition. The cellular component of the meniscus is zone-specific, comprising both fibrochondrocytes and chondrocyte-like cells.

The composition of the meniscus differs in each zone. In the outer red-red zone, the cells are more fibroblast-like in morphology, with many processes. The ECM in this zone is mainly fibrillar collagen type-I (80%). The inner white-white zone has ECM closely resembling hyaline cartilage, with more collagen-II (42%), a reduced proportion of collagen-I (28%) and a higher GAG concentration. The cells in this zone are termed fibrochondrocytes, or chondrocyte-like cells. The superficial layers of the menisci have another distinct cell type with potential stem cell-like properties. The zone-specific ECM components of the meniscus are generated by the cells resident within the tissue, thus phenotypic markers for meniscal cells can include ECM protein expression or gene expression such as: COL1A1 (collagen-1), COL2A2 (collagen-2), VCAN (versican), ACAN (aggrecan), CSPG4 (chondroitin-6-sulfate), Sox9 and Col10a (collagen-10a). Similar to the unique cell types in each meniscal zone, cell density also varies in each zone. Vascular (red-red) and avascular (white-red, white-white) zones have average cell densities of 12,820 cells/mm$^3$ and 27,199 cells/mm$^3$, respectively, and more fibrochondrocytes than fibroblast-like cells (Cengiz et al., 2015). The meniscus is highly heterogenous, with zone-specific variation in cell phenotype and ECM composition.

The heterogeneous distribution of cell types and biochemical scaffold content of the knee meniscus is described in Table 1. The red-red zone is characterised by fibroblast-like cells and a collagen-I-predominant extracellular matrix (ECM), with trace amounts of collagen-II. The white-red and white-white zones contain fibrochondrocyte cells and a matrix rich in collagen-II, and a higher proportion of glycosaminoglycans (GAGs).

TABLE 1

| Organic component | Zone | | |
|---|---|---|---|
| | Red-Red zone | Red-white zone | White-White zone |
| Cells | Vessels, nerves, & fibroblast-like cells | Fibrochondrocytes/ Chondrocyte-like cells | Fibrochondrocytes & superficial zone cells (stem cells) |
| ECM (% total dry wgt) | | | |
| Total collagen | >80% | 70% | 70% |
| Collagen-I | >80% | 28% | 28% |
| Collagen-II | <1% | 42% | 42% |
| Collagens-III, IV, V, VI, XVIII, fibronectin, thrombospondin | <1% | <1% | <1% |
| Elastin | <0.6% | <0.6% | <0.6% |
| GAGs (% total dry wgt) | | | |
| Total GAGs | 17% | 30% | 30% |
| Chondroitin-6-sulfate | 10.2% | 18% | 18% |
| Dermatan sulfate | 3.4-5.1% | 6.0-9.0% | 6.0-9.0% |
| Chondroitin-4-sulfate | 1.7-3.4% | 3.0-6.0% | 3.0-6.0% |
| Keratin sulfate | 2.6% | 4.5% | 4.5% |

Collagen Fiber Patterning Confers Meniscal Biomechanical Properties

Figure 4:
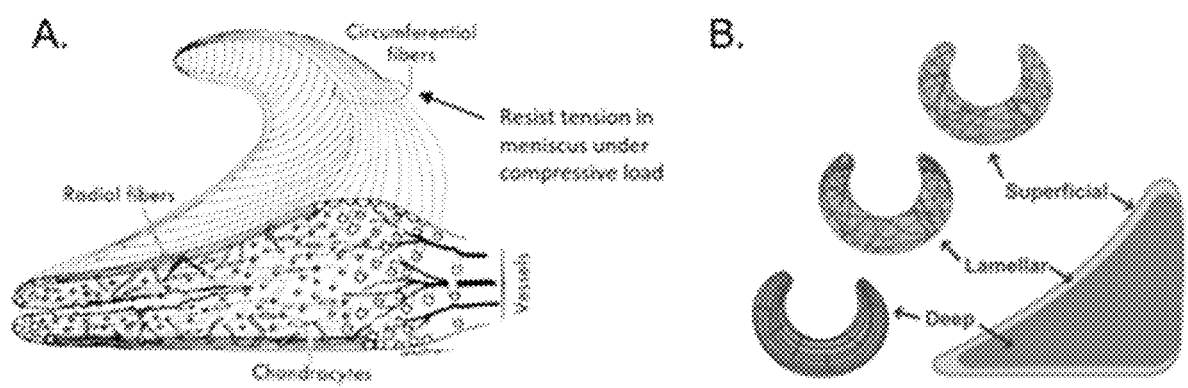
FIG. 4, Panel A is a schematic illustration of a meniscus, depicting a cross sectional view. Circumferential and radial alignment of collagen fibers confer biomechanical properties to the meniscus. Panel B depicts a superficial zone, a lamellar zone, and an interior (deep) zone. Collagen fibers in the superficial and lamellar zones close to the meniscus surface are randomly oriented. Fibers deeper in the meniscus are oriented in both circumferential and radial directions.
Figure 5:
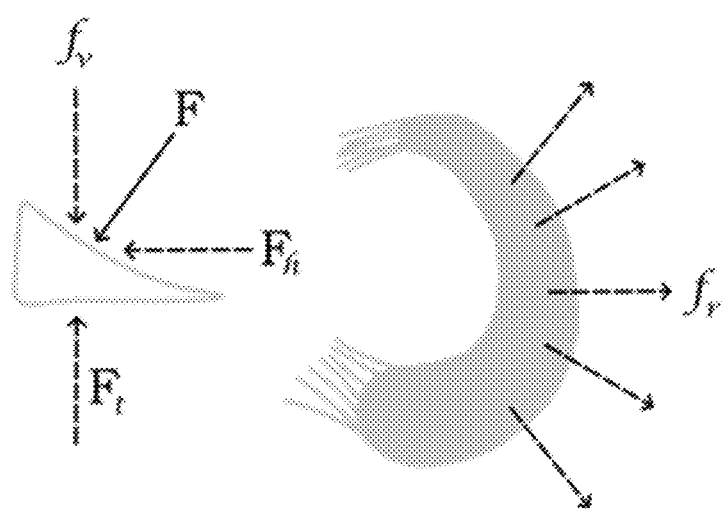
FIG. 5 is a force diagram that depicts the components of an axial load force F on various portions of a meniscus. The axial load force (F) perpendicular to the meniscus surface and horizontal force ($f_r$) are created by compressing the femur ($F_f$). F rebounds due to the tibial upgrade force ($F_t$), whereas $f_r$ leads to meniscal extrusion radially, which is countered by the pulling force from the anterior and posterior insertional ligaments. Consequently, tensile hoop stress is created along the circumferential directions during axial compression, which is resisted by the circumferentially-oriented collagen fibers. (Adapted from: The knee meniscus: structure-function, pathophysiology, current repair techniques, and prospects for regeneration. Biomaterials. 2011 October; 32(30): 7411-7431. doi:10.1016/j.biomaterials.2011.06.037, Eleftherios A. Makris, MD1, Pasha Hadidi, BS1, and Kyriacos A. Athanasiou, Ph.D., P.E.1).

The micro-anatomic geometry of the meniscus is closely associated with its biomechanical properties. The hydrated nature of the meniscus (~72% water) confers resistance to compressive stress, as water is incompressible, however, the meniscus has considerable tensile strength which is conferred via the ordered arrangement of 10 μm-diameter collagen fibers throughout the tissue (FIG. 4) (Baker et al., 2007). The surface and lamellar zones of the meniscus are made up of randomly oriented collagen fibers, whereas the fibers deeper in the meniscus are oriented in circumferential and radial directions. With normal use, forces of several times body weight arise within the knee, with the menisci transmitting 50-100% of this load through the dense network of circumferentially aligned collagen fibers (FIG. 4). This ordered architecture engenders very high tensile properties in the fiber direction (50-300 MPa) (Baker et al., 2007). Tensile hoop stress is created in the circumferential direction when the knee bears an axial load, and this stress tries to extrude the meniscus out of the knee joint (FIG. 5). However, the tensile strength of circumferentially-aligned collagen fibers and the firm attachment at the anterior and posterior insertional ligaments helps prevent extrusion of the meniscus and significantly reduces stress and protects the tibial cartilage. In contrast, if the anterior or posterior insertional ligaments or peripheral circumferential collagen fibers rupture, the load transmission mechanism changes, which damages the tibial cartilage. Compressive strength has been measured in fresh-frozen cadaveric human menisci, the axial and radial compressive moduli at 12% strain were 83.4 kPa and 76.1 kPa, respectively, with tensile modulus several orders of magnitude greater (Chia & Hull, 2008).

The goal of tissue engineering is to generate a structure that recapitulates the function of the native tissue. In the case of the meniscus, the challenge is to generate a living tissue capable of long-term engraftment into the knee joint, while also having the biomechanical strength necessary to withstand the considerable compressive forces that it is exposed to during everyday life. The meniscus is a surprisingly complex tissue with specific architecture at the mm, μm and nm scale, all of which contribute to the biomechanical function of the tissue. To date, meniscal engineering has been somewhat limited by the fabrication tools available to researchers, such as molding hydrogels using casts, or seeding cells onto prefabricated scaffolds. These approaches are not capable of generating the micro-scale architectures necessary to recapitulate function. In contrast, the meniscus implants described herein are able to achieve point to point control over matrix material(s), cell type, cell density, and active agent composition, which facilitates the generation of an implant that more closely resembles native structural features of the meniscus.

Figure 6:
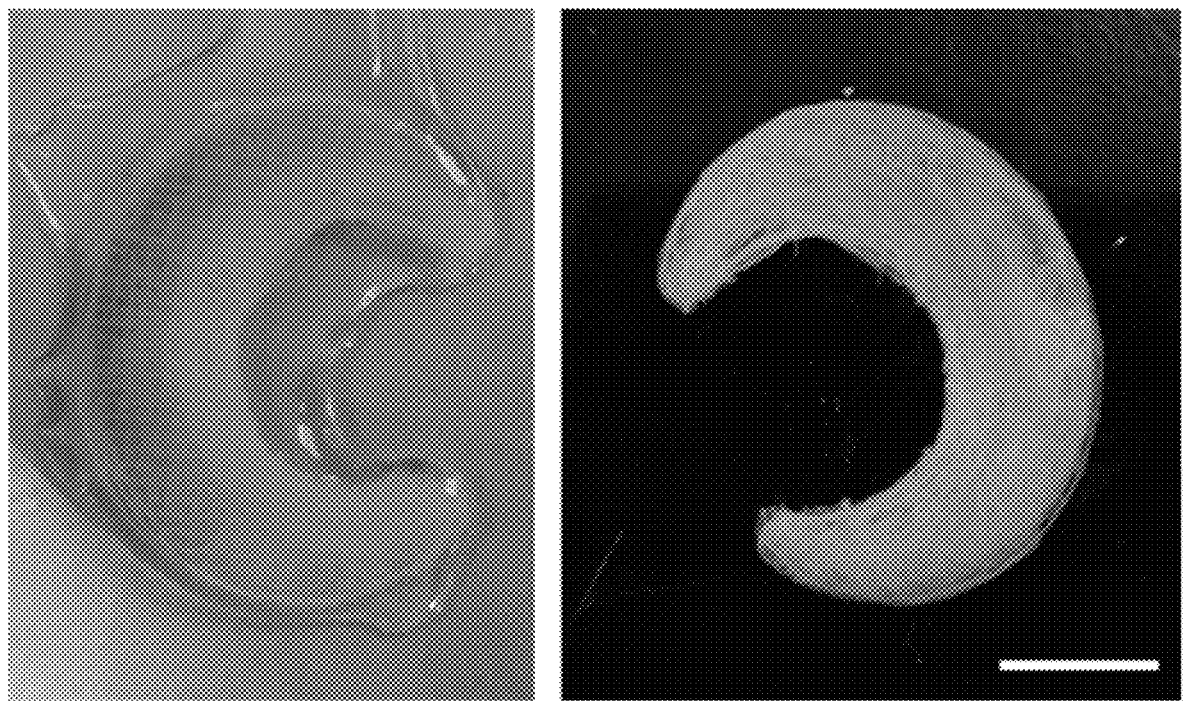
FIG. 6 provides images of two cell-free 3D meniscus-like structures with pre-programmed zone-specific scaffold content and coordinated patterning of printed synthetic tissue fiber structures. Scale bar=1 cm.

The meniscus is a heterogeneous tissue, with cells and ECM components distributed in specific zones. Zonal specificity is vital for conferring regenerative and biomechanical function. The subject artificial meniscus implants employ specific placement of different matrix materials, cell types, cell densities, and active agent compositions into precise regions and/or zones of the 3D tissue, thus allowing for re-creation of the red-red, white-red, white-white zonal architecture of the meniscus (FIG. 6).

The density of cells within the human meniscus has been demonstrated to vary in a zone-specific manner (approximately $13 \times 10^6$ cells/ml in the red-red zone, and $28 \times 10^6$ cells/ml in the white-white and white-red zones (Cengiz et al., 2015)). Cell density plays a vital role in maintaining appropriate cell phenotype, ECM organization and corresponding tissue biomechanics. In some embodiments, the subject meniscus implants comprise cell densities ranging from about 0 to about $100 \times 10^6$ cells/mL or more. As such, in some embodiments, the subject meniscus implants can have a cell density that varies from one position within the implant to another. For example, in certain embodiments, a meniscus implant comprises a layer having a cell density that varies in at least one direction. In other embodiments, the subject implants are acellular and designed for endogenous cell ingrowth.

Collagen gives most tissues tensile strength, and multiple collagen fibrils approximately 100 nm in diameter combine to generate strong coiled-coil fibers of approximately 10 μm in diameter. Biomechanical function of the meniscus is conferred via collagen fiber alignment in circumferential and radial directions (FIG. 4). In some embodiments, the subject meniscus implants comprise patterned collagen fibrils that are created by modulating the diameter of the synthetic tissue fiber structures that are used to create the implant.

Figure 7:
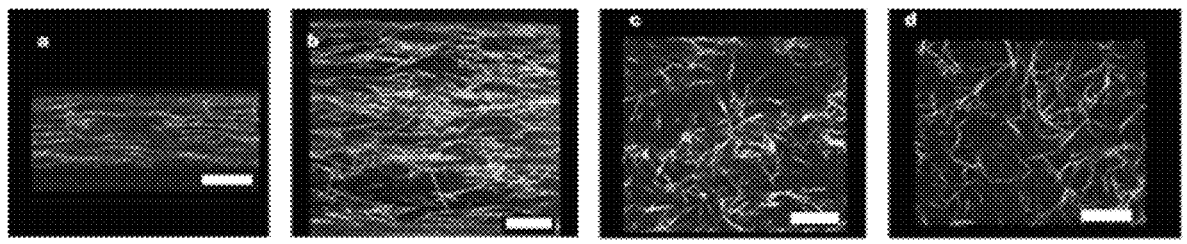
FIG. 7 is a series of microscope images that depict spontaneous collagen fiber alignment in small diameter fibers. Polymerised collagen fiber orientation in microfluidic channels of different diameters including; 30 um (Panel a), 100 um (Panel b), 400 um (Panel c) and no channel (Panel d) (Lee et al., 2006).
Figure 8:
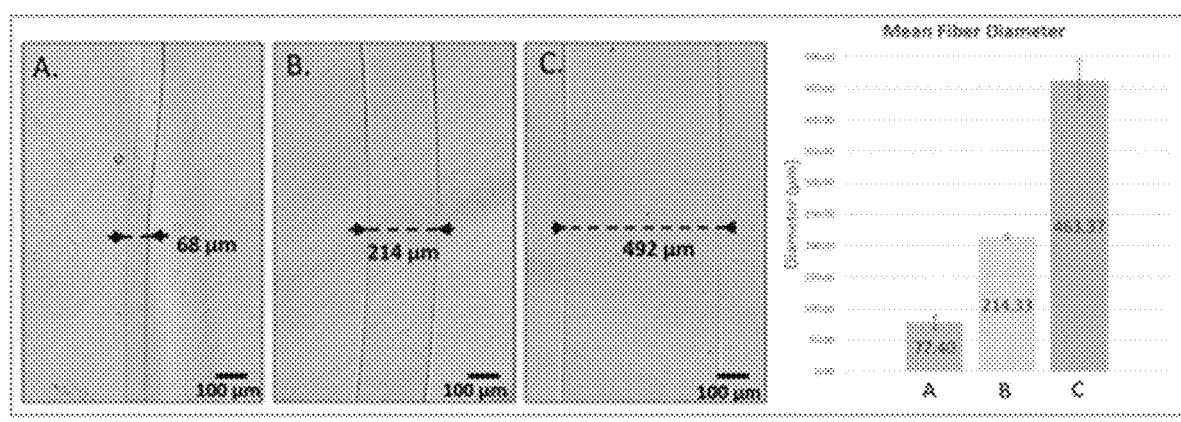
FIG. 8 shows a series of images showing on-the-fly modulation of printed alginate-based fiber diameter using a 3D bioprinting system, as well as a graph comparing the mean fiber diameters. Panels A, B, and C depict alginate-based fibers of 3 different diameters that were generated by printing at 3 different pressure settings in the 3D bioprinting system. Quantification of width in multiple fibers demonstrates that the mean diameter at each pressure setting is consistent (graph, right).

Previous studies have shown that microfluidic channels of different diameters can direct the polymerization of collagen fibrils to form fibers that are oriented along the length of the channels, but only at channel diameters of 100 μm or less (Lee et al., 2006) (FIG. 7). Primary endothelial cells grown in these oriented matrices were shown to align in the direction of the collagen fibers. In another study, Martinez et al, demonstrate that 500 μm channels within a cellulose-bead scaffold can direct collagen and cell alignment (Martinez et al., 2012). In some embodiments, the subject meniscus implants comprise synthetic tissue fiber structures that have a diameter that ranges from about 20 μm to about 500 μm, such as about 50 μm, about 75 μm, about 100 μm, about 125 μm, about 150 μm, about 175 μm, about 200 μm, about 225 μm, about 250 μm, about 275 μm, about 300 μm, about 325 μm, about 350 μm, about 375 μm, about 400 μm, about 425 μm, about 450 μm, or about 475 μm (FIG. 7). By modulating the fiber diameter, the orientation of the collagen fibers within the subject meniscus implants can be controlled. As such, the synthetic tissue fiber structures, and the collagen fibers within them, can therefore be patterned to produce meniscus implants with a physiologically accurate arrangement of circumferential and radially aligned collagen fibers, essential for conferring necessary biomechanical properties on the meniscus implants (FIG. 8).

The meniscus is an intrinsically heterogeneous structure with zones of varying composition and architecture. The subject meniscus implants comprise complex biological structures that comprise unique material compositions and architectures, including, without limitation, fiber diameter, ECM composition, cell composition, and cell density. The ability to control these and other aspects of the synthetic tissue fiber structures that are used to generate the subject meniscus implants enables construction of the zonal architectures found in native meniscus tissue.

In certain embodiments, the subject meniscus implants are generated using automated control systems that modulate one or more characteristics of the synthetic tissue fiber(s) to achieve, e.g., material switching within an individual fiber structure, between separate fiber structures, within or across a layer, within or across a zone, and essentially at any point throughout the structure. As a result, point to point control of the meniscus implant composition is achieved. Furthermore, key parameters, such as fiber diameter and layer thickness, can also be modulated as desired. This level of automated control is essential to accurately recreating the heterogeneous composition and morphology found in native knee menisci.

The subject synthetic tissue fibers support the viable growth of a wide variety of human cells. The synthetic tissue fiber structures can be finely tuned to contain, e.g., different ECM proteins, GAGs and growth factors to optimize the matrix for specific cell types. Computer-controlled deposition of the synthetic tissue fiber structures enables precise placement of cells and matrix materials into specific locations to generate physiologically-relevant heterogeneous meniscus implants.

In certain embodiments, the mechanical properties of a meniscus implant are controlled by modulating the patterning of collagen, and/or by modulating one or more characteristics of the matrix materials (e.g., alginate, collagen) that are used to generate the synthetic tissue fiber structures. For example, in some embodiments, one or more anchor regions, as described above, are placed about the periphery of an implant to facilitate attachment and/or fixation, e.g., via suturing or the like. Anchor regions can be generated by the incorporation of higher strength materials, for example, stiffer synthetic materials, including, but not limited to, polycaprolactone (PCL), poly(lactic-co-glycolic acid) (PLGA), polyurethane (PU) or any combination thereof. Anchor regions in accordance with embodiments of the invention can contain, e.g., double network hydrogels, generated by combining at least two different hydrogel materials including, but not limited to: alginate, Gelatin methacrylol (GelMA), methacryloyl polyethylene glycol (PEGMA), gellan gum, agarose, polyacrylamide, or any combination thereof. In addition, high strength fibers may be generated from high concentrations of biological polymers, including, but not limited to: collagen, chitosan, silk fibroin, or any combination thereof, and these may be incorporated into one or more anchor regions.

Artificial meniscus implants in accordance with embodiments of the invention can include from 0 to about 12 anchor regions, such as 1, 2, 3, 4, 5, 6, 7, 8, 9, 10 or 11 anchor regions. Anchor regions in accordance with embodiments of the invention can range in size from about 5 mm$^2$ to about 40 mm$^2$, such as about 6, 7, 8, 9 or 10 mm$^2$, or about 12, 14, 16, 18, 20, 22, 24, 26, 28, 30, 32, 34, 36 or 38 mm$^2$.

Anchor regions in accordance with embodiments of the invention can be generated by the incorporation of higher strength materials into suture points, for example, stiffer synthetic materials such as, e.g., polycaprolactone (PCL), poly(lactic-co-glycolic acid) (PLGA), polyurethane (PU), or any combination thereof. Anchor regions in accordance with embodiments of the invention can optionally contain double network hydrogels, generated by combining at least two different hydrogel materials, including but not limited to, alginate, Gelatin methacrylol (GelMA), methacryloyl polyethylene glycol (PEGMA), gellan gum, agarose, polyacrylamide, or any combination thereof. In addition, high strength fibers can be generated from high concentrations of biological polymers, including, but not limited to, collagen, chitosan, silk fibroin, or any combination thereof. In some embodiments, one or more of these biological polymers can be incorporated into one or more anchor regions. In some embodiments, the entire periphery of a layer of an artificial meniscus implant comprises a reinforced matrix material. In some embodiments, the periphery comprises a plurality of reinforced anchor regions comprising one or more reinforced matrix materials.

In some embodiments, high strength fibers can be incorporated (e.g., patterned) into one or more reinforced peripheral regions of an artificial meniscus implant to increase strength along the periphery of the implant. In some embodiments, high strength fibers are incorporated into the entire periphery of the implant. Within an anchor region and/or a reinforced peripheral region of an artificial meniscus implant, layers of high strength material can be alternated with layers of softer material that is optimized for cell survival and ingrowth. Increased strength within anchor regions and/or reinforced peripheral region can be conferred by increasing the concentration of a fiber material, by increasing the infill density of the printed fibers, by increasing the diameter of the printed fibers, or by any combination thereof. In some embodiments, an anchor region can be colored by incorporating, e.g., a non-toxic dye into the printable anchor material to act as a visual guide during surgery, thereby informing the surgeon of the location of the reinforced areas of the artificial meniscus implant that are adapted for placement of sutures.

In the human meniscus, the correct orientation and alignment of collagen fibers is crucial to confer appropriate biomechanical properties to the tissue. As discussed previously, spontaneous collagen fiber orientation and subsequent cell alignment can be directed by restricting the cross-linking process to small diameter channels or fibers less than approximately 100 µm (Lee et al., 2006) (Onoe et al., 2006). In certain embodiments, the subject meniscus implants comprise a layer wherein one or more synthetic tissue fiber structures are configured to promote deposition of collagen fibers that are aligned with a longitudinal direction of the synthetic tissue fiber. As such, in certain embodiments, a synthetic tissue fiber(s) is deposited in a radial and/or a circumferential orientation, and is configured to promote deposition of collagen fibers that are aligned with the radial and/or circumferential directional orientation of the synthetic tissue fiber(s). In this way, circumferential and/or radial orientation of collagen fibers can be achieved.

Figure 9:
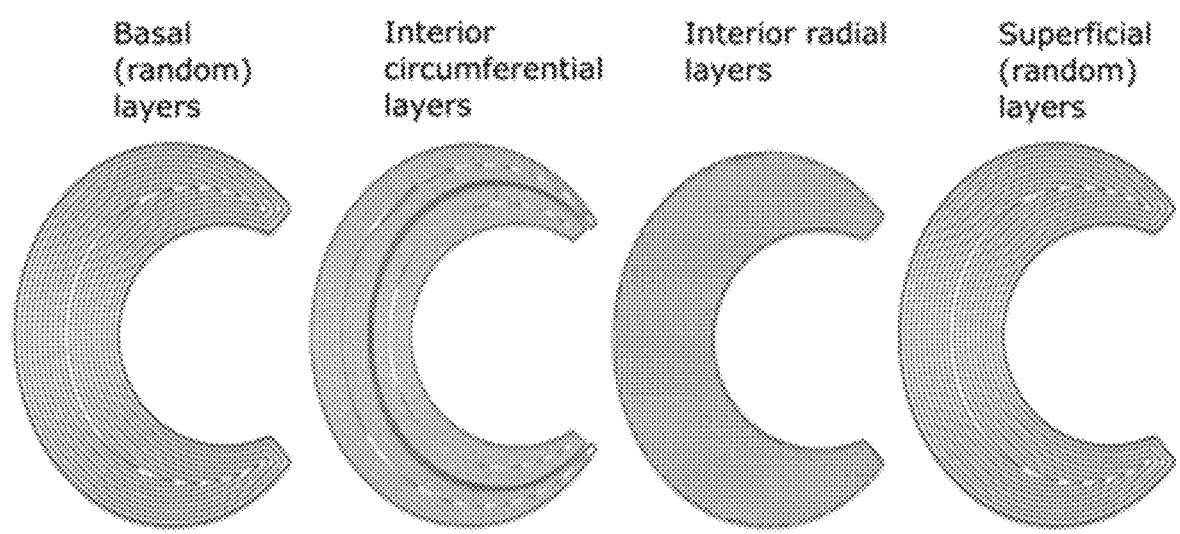
FIG. 9 is an illustration of synthetic tissue fiber patterning in various layers of a 3D bioprinted meniscus. Synthetic tissue fiber structures of specific diameters loaded with extracellular matrix (ECM), e.g., collagen, are patterned in a manner that recapitulates the micro-patterning of collagen and the zonal architecture of the meniscus. The basal and superficial zones contain randomly oriented fibers printed in larger diameter fibers. The interior zones contain circumferential and radially-aligned collagens aligned within patterned fibers of smaller diameter.

In some embodiments, the diameter of a synthetic tissue fiber is modulated so that collagen fibers are aligned appropriately; e.g. the surface and periphery of the meniscus contain randomly-oriented (e.g., disordered) collagen fibers, whereas the inner region(s) contain circumferentially and radially-aligned fibers. An illustration of a non-limiting example of the synthetic tissue fiber orientation in each of a plurality of layers in a subject meniscus implant is shown in FIG. 9.

Meniscus Injury and Options for Surgical Repair

Damage to the meniscus is very common in the knee joint. Meniscal lesions are typically categorized by distinct age groups. Meniscal injuries in younger human patients (<40 years) are usually caused by trauma or congenital meniscal diseases, whereas those in older human patients (>40 years) tend to be associated with degenerative tears. Meniscal injuries can simply be classified clinically into peripheral meniscal lesions and avascular meniscal lesions. Numerous surgical techniques have been developed to repair meniscal tears in the vascular (red-red) zone with high overall success rates in young patients with stable knees (63-91%). Damage and tearing in the avascular (white-white) zone of the meniscus are often associated with a poor prognosis following repair and consequently several different therapeutic strategies have been attempted with varied results. The most notable include the use of parameniscal synovial tissue, trephination of the peripheral meniscus rim with suture of the meniscus tear, creation of vascular access channels, and the use of mesenchymal stem cells and/or growth factors. None of the above techniques have been generally adopted, thus the main strategy of orthopedic surgeons is to perform a partial meniscectomy in cases of unrepairable or degenerative meniscal injuries, even though this treatment strategy does not prevent the development of knee OA. A partial meniscectomy can result in OA by decreasing the contact area between the femoral condyle and tibial platform. Altering the loading characteristics of the articular knee cartilage can lead to progressive degeneration of meniscus and articular cartilage via a vicious cycle of damage, inflammation and further tissue degeneration.

Artificial Meniscus Implants:

As reviewed above, aspects of the invention include artificial meniscus implants comprising at least one basal zone, at least one interior zone, and at least one superficial zone, wherein each of said zone comprises a layer comprising at least one synthetic tissue fiber dispensed from a bioprinter as a solidified biocompatible matrix optionally comprising cells, and optionally comprising one or more active agents, as described herein. In some embodiments, one or more of the matrix material, cell type, cell density, and/or type and/or amount of an active agent can vary can vary across at least one direction of a given layer. For example, in some embodiments, a layer of a meniscus implant can have a cell density that is lower along a first side, and increases (in a linear or non-linear manner) across the layer towards the opposite side. In certain embodiments, the cell density in a given layer can vary in two directions. For example, in some embodiments, the cell density in a given layer can increase (in a linear or non-linear manner) in both an x- and a y-direction across the layer. In certain embodiments, the cell density can vary from 0 to $100 \times 10^6$ cells per mL, or more.

In some embodiments, at least one layer of the subject artificial meniscus implant can comprise at least one circumferentially and/or radially oriented synthetic tissue fiber. The circumferential and/or radial fiber(s) can have the same or different diameters, the same or different matrix materials, the same or different cell types, and the same or different cell densities. In certain embodiments, the diameter of a synthetic tissue fiber can vary from 20 μm to 500 μm.

Figure 10:
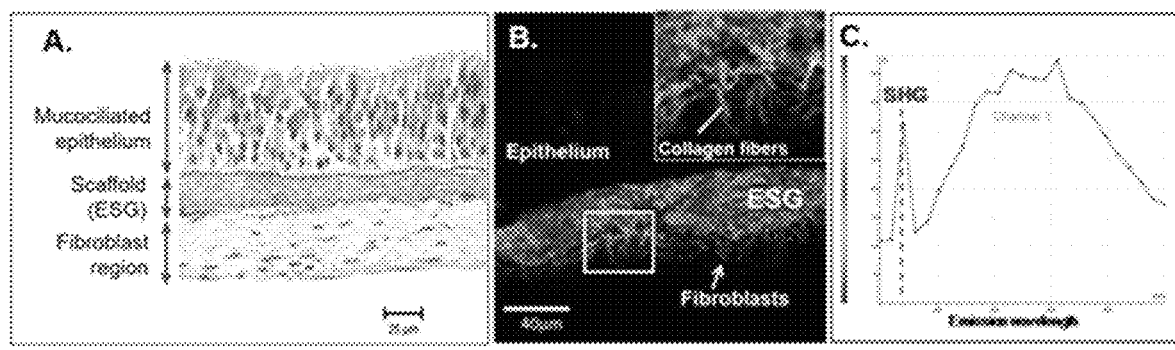
FIG. 10 shows data from 2-photon imaging of collagen fibers in an engineered 3D tissue. Panel A: formaldehyde-fixed, H&E stained section of a 3D co-culture of primary human airway epithelial cells and fibroblasts after 90 day culture on an electrospun gelatin (ESG) scaffold. Panel B: 2-photon imaging of unstained sections demonstrating deposition of fibrillar collagen (purple) oriented parallel to the surface of the ESG scaffold, in a similar direction to the fibroblasts depositing the collagen. Panel C: Emission spectra of the unstained tissues demonstrates that non-centrosymmetric collagen fibers generate a specific $2^{nd}$ harmonic signal (SHG) (Wadsworth et al., 2014).

In certain embodiments, a synthetic tissue fiber is configured to promote deposition of collagen fibers aligned with a longitudinal direction of the synthetic tissue fiber. In certain embodiments, a synthetic tissue fiber is configured to promote deposition of randomly-oriented collagen fibers. As provided in FIG. 10, collagen fibers in 3D engineered tissues take on an orientation dependent on one or more features of the scaffold materials used to create the 3D tissue. Similarly, aspects of the subject artificial meniscus implants can be modulated to control the orientation of the collagen fibers within the implant material.

Figure 11:
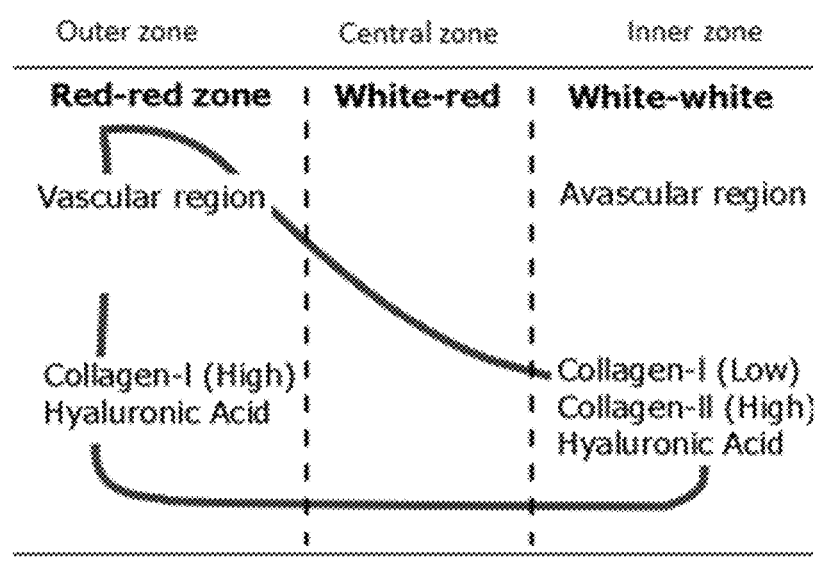
FIG. 11 is an illustration of a meniscal tissue with zone-specific cell and ECM content. "Red-Red bio-ink" and "White-white bio-ink" are used to generate tissues with zonal architecture. Desired cell types, (e.g., MSC-derived chondrocytes or primary meniscus-derived cells) are seeded at appropriate physiological densities into red-red and white-white zones. Specific ECM content of the scaffold is modified according to the tissue zone. The "white-red" zone in the central zone of the tissue contains a mixture of red-red and white-white bio-inks and cells. The bioprinting system facilitates control over both the cellular (cell type and cell density) and ECM content in any given zone of the meniscus implant.

In certain embodiments, a subject meniscus implant is constructed, using sequential deposition of layers, as described above, such that the meniscus implant comprises an inner, central and outer zone, as provided in FIG. 11. In certain embodiments, the cell type, cell density, and/or matrix material present in any given zone can be controlled, thereby creating a meniscus implant that resembles the native architecture and biomechanical characteristics of natural meniscus tissue.

Biocompatible Matrix Materials:

The solidified biocompatible matrix may comprise any of a wide variety of natural or synthetic polymers that support the viability of living cells, including, e.g., alginate, laminin, fibrin, hyaluronic acid, poly(ethylene) glycol based gels, gelatin, chitosan, agarose, or combinations thereof. In preferred embodiments, the solidified biocompatible matrix comprises alginate, or other suitable biocompatible polymers that can be instantaneously solidified while dispensing from the printhead. In further preferred embodiments, the solidified biocompatible matrix comprises a homogeneous composition of alginate throughout the radial cross section of each synthetic tissue fiber.

In particularly preferred embodiments, the solidified biocompatible matrix is physiologically compatible, i.e., conducive to cell growth, differentiation and communication. By "physiological matrix material" is meant a biological material found in a native mammalian tissue. Non-limiting examples of such physiological matrix materials include: fibronectin, thrombospondin, glycosaminoglycans (GAG) (e.g., hyaluronic acid, chondroitin-6-sulfate, dermatan sulfate, chondroitin-4-sulfate, or keratin sulfate), deoxyribonucleic acid (DNA), adhesion glycoproteins, and collagen (e.g., collagen I, collagen II, collagen III, collagen IV, collagen V, collagen VI, or collagen XVIII).

Mammalian Cell Types:

Non-limiting examples of mammalian cells types that can be used in the subject meniscus implants include: fibroblasts, chondrocytes, meniscus fibrochondrocytes, stem cells, bone marrow stromal (stem) cells, embryonic stem cells, mesenchymal stem cells, induced pluripotent stem cells, differentiated stem cells, tissue-derived cells, smooth muscle cells, skeletal muscle cells, epithelial cells, endothelial cells, myoblasts, chondroblasts, osteoblasts, osteoclasts, and any combinations thereof.

Cells can be obtained from donors (allogenic) or from recipients (autologous). Cells can also be from established cell culture lines, or can be cells that have undergone genetic engineering and/or manipulation to achieve a desired genotype of phenotype. In some embodiments, pieces of tissue can also be used, which may provide a number of different cell types in the same structure. In one preferred embodiment, the artificial meniscus implant comprises patient-specific bone marrow-derived mesenchymal stem cells. In one preferred embodiment, the artificial meniscus implant comprises primary meniscal chondrocytes. In one preferred embodiment, the artificial meniscus implant comprises microvascular endothelial cells. In one preferred embodiment, the artificial meniscus implant comprises patient-specific induced pluripotent stem cell derived chondrocytes.

In some embodiments, cells can be obtained from a suitable donor, either human or animal, or from the subject into which the cells are to be implanted. Mammalian species include, but are not limited to, humans, monkeys, dogs, cows, horses, pigs, sheep, goats, cats, mice, rabbits, rats. In one embodiment, the cells are human cells. In other embodiments, the cells can be derived from animals such as, dogs, cats, horses, monkeys, or any other mammal.

Without being held to any particular theory, the number of cells seeded does not limit the final tissue (e.g., meniscus) produced, however, optimal cell density can improve one or more properties of the subject meniscus implants.

Cells can be present anywhere within a meniscus implant, e.g., within the basal zone, within the interior zone, and/or within the superficial zone. In some embodiments, to mimic native meniscus fibrocartilaginous structure, different types of cells can be spatially placed in certain zones of the meniscus implant. For example, in some embodiments, one or more fibroblasts can be placed in a first region and/or in the individual layers of the meniscus implant. In some embodiments, one or more chondrocytes can be placed in a first region and/or in the individual layers of the meniscus implant.

Cells of a particular type, and having a particular density, can be placed into any desired zone of the subject meniscus implants. In some embodiments, one or more stem cells, e.g., bone marrow stem cells, can be placed within at least a portion of a subject meniscus implant and/or the individual layers thereof. In some embodiments, at least a portion of the stem cells can be differentiated to a chondrogenic phenotype. One of ordinary skill in the art can readily perform differentiating stem cells into a desired phenotype (e.g., a chondrogenic phenotype) e.g., by exposing the cells to art-recognized cell differentiation factors and/or commercially-available differentiation media.

Appropriate growth conditions for mammalian cells are well known in the art (Freshney, R. I. (2000) Culture of Animal Cells, a Manual of Basic Technique. Hoboken N.J., John Wiley & Sons; Lanza et al. Principles of Tissue Engineering, Academic Press; 2nd edition May 15, 2000; and Lanza & Atala, Methods of Tissue Engineering Academic Press; 1st edition October 2001). Cell culture media generally include essential nutrients and, optionally, additional elements such as growth factors, salts, minerals, vitamins, etc., that may be selected according to the cell type(s) being cultured. Particular ingredients may be selected to enhance cell growth, differentiation, secretion of specific proteins, etc. In general, standard growth media include Dulbecco's Modified Eagle Medium, low glucose (DMEM), with 110 mg/L pyruvate and glutamine, supplemented with 10-20% fetal bovine serum (FBS) or calf serum and 100 U/ml penicillin are appropriate as are various other standard media well known to those in the art. Growth conditions will vary dependent on the type of mammalian cells in use and tissue desired.

Additional sources of human cells include, but are not limited to, bone marrow-derived mesenchymal stem cells (MSCs) and primary human meniscus-derived chondrocytes. MSCs are attractive for regenerative medicine purposes as they can be isolated from patients and readily expanded for use as an autograft tissue replacement. Unlike donor allografts, recipient-derived MSC autografts have zero risk of inter-person disease transmission or immune-mediated tissue rejection. An additional advantage of MSCs is that the culture protocols to differentiate MSCs into fibrochondrocyte-like cells are well defined. Chemically defined medium has been demonstrated to induce a chondrogenic phenotype in cultured MSCs as well as promote deposition of fibrocartilaginous ECM by MFCs in pellet culture over a 10-week period (Mauck 2006 & Brendon 2007).

The de-differentiation of chondrocytes in 2D cell culture conditions has encouraged investigation into the effects of more complex physiological culture conditions. Oxygen has a fundamental effect on cell behavior and the cells of the avascular zone of the meniscus are under low oxygen conditions due to the lack of oxygenated blood supply. Several studies have investigated the effects of hypoxic growth conditions on chondrocyte phenotype; bovine articular chondrocytes grown in hypoxic (5% $O_2$) culture were shown to re-express high amounts of collagen-II at the protein level compared to the same cells grown in normoxic (21% 02) conditions (Domm et al., 2002). The meniscus is under regular compressive stress, and it has been postulated that mechanical stimulation is necessary to trigger appropriate chondrocyte phenotype. Ultrasonic stimulation at a frequency of 1 MHz was demonstrated to increase the deposition of ECM by chondrocytes in 2D and 3D cultures, but the effect was transient only lasting for 28 days (Hsu et al., 2006). Upton et al., isolated cells from the inner and outer zones of the meniscus and grew them in monolayers on flexible membranes. When exposed to a biaxial strain of 5% both populations of cells were shown to increase NO and total protein expression (Upton et al., 2006). For optimal meniscus biomechanical performance, hypoxic culture and mechanical strain can be utilized to maximize phenotypic differentiation of MSC-derived chondrocytes or primary meniscal cells in 3D cultures.

Active Agents:

In some aspects, a meniscus implant in accordance with embodiments of the invention can comprise at least one active agent. Non-limiting examples of such active agents include TGF-β1, TGF-β2, TGF-β3, BMP-2, BMP-4, BMP-6, BMP-12, BMP-13, basic fibroblast growth factor, fibroblast growth factor-1, fibroblast growth factor-2, platelet-derived growth factor-AA, platelet-derived growth factor-BB, platelet rich plasma, IGF-I, IGF-II, GDF-5, GDF-6, GDF-8, GDF-10, vascular endothelial cell-derived growth factor, pleiotrophin, endothelin, nicotinamide, glucagon like peptide-I, glucagon like peptide-II, parathyroid hormone, tenascin-C, tropoelastin, thrombin-derived peptides, laminin, biological peptides containing cell-binding domains and biological peptides containing heparin-binding domains, therapeutic agents, and any combinations thereof.

The term "therapeutic agents" as used herein refers to any chemical moiety that is a biologically, physiologically, or pharmacologically active substance that acts locally or systemically in a subject. Non-limiting examples of therapeutic agents, also referred to as "drugs", are described in well-known literature references such as the Merck Index, the Physician's Desk Reference, and The Pharmacological Basis of Therapeutics, and they include, without limitation, medicaments; vitamins; mineral supplements; substances used for the treatment, prevention, diagnosis, cure or mitigation of a disease or illness; substances which affect the structure or function of the body; or pro-drugs, which become biologically active or more active after they have been placed in a physiological environment. In some embodiments, one or more therapeutic agents can be used, which are capable of being released from a meniscus implant described herein into adjacent tissues or fluids upon implantation to a subject. Examples of therapeutic agents include, but are not limited to, antibiotics, anesthetics, any therapeutic agents that promote meniscus regeneration or tissue healing, or that reduce pain, infection, or inflammation, or any combination thereof.

Additional active agents can include, but are not limited to, proteins, peptides, nucleic acid analogues, nucleotides, oligonucleotides, nucleic acids (DNA, RNA, siRNA), peptide nucleic acids, aptamers, antibodies or fragments or portions thereof, antigens or epitopes, hormones, hormone antagonists, growth factors or recombinant growth factors and fragments and variants thereof, cytokines, enzymes, antibiotics or antimicrobial compounds, anti-inflammation agent, antifungals, antivirals, toxins, prodrugs, small molecules, drugs (e.g., drugs, dyes, amino acids, vitamins, antioxidants) or any combination thereof.

Non-limiting examples of antibiotics that are suitable for inclusion in a meniscus implant of the present invention include: aminoglycosides (e.g., neomycin), ansamycins, carbacephem, carbapenems, cephalosporins (e.g., cefazolin, cefaclor, cefditoren, cefditoren, ceftobiprole), glycopeptides (e.g., vancomycin), macrolides (e.g., erythromycin, azithromycin), monobactams, penicillins (e.g., amoxicillin, ampicillin, cloxacillin, dicloxacillin, flucloxacillin), polypeptides (e.g., bacitracin, polymyxin B), quinolones (e.g., ciprofloxacin, enoxacin, gatifloxacin, ofloxacin, etc.), sulfonamides (e.g., sulfasalazine, trimethoprim, trimethoprim-sulfamethoxazole (co-trimoxazole)), tetracyclines (e.g., doxycyline, minocycline, tetracycline, etc.), chloramphenicol, lincomycin, clindamycin, ethambutol, mupirocin, metronidazole, pyrazinamide, thiamphenicol, rifampicin, thiamphenicl, dapsone, clofazimine, quinupristin, metronidazole, linezolid, isoniazid, fosfomycin, fusidic acid, or any combination thereof.

Non-limiting examples of antibodies include: abciximab, adalimumab, alemtuzumab, basiliximab, bevacizumab, cetuximab, certolizumab pegol, daclizumab, eculizumab, efalizumab, gemtuzumab, ibritumomab tiuxetan, infliximab, muromonab-CD3, natalizumab, ofatumumab omalizumab, palivizumab, panitumumab, ranibizumab, rituximab, tositumomab, trastuzumab, altumomab pentetate, arcitumomab, atlizumab, bectumomab, belimumab, besilesomab, biciromab, canakinumab, capromab pendetide, catumaxomab, denosumab, edrecolomab, efungumab, ertumaxomab, etaracizumab, fanolesomab, fontolizumab, gemtuzumab ozogamicin, golimumab, igovomab, imciromab, labetuzumab, mepolizumab, motavizumab, nimotuzumab, nofetumomab merpentan, oregovomab, pemtumomab, pertuzumab, rovelizumab, ruplizumab, sulesomab, tacatuzumab tetraxetan, tefibazumab, tocilizumab, ustekinumab, visilizumab, votumumab, zalutumumab, zanolimumab, or any combination thereof.

Non-limiting examples of enzymes suitable for use in a meniscus implant as described herein include: peroxidase, lipase, amylose, organophosphate dehydrogenase, ligases, restriction endonucleases, ribonucleases, DNA polymerases, glucose oxidase, and laccase.

Additional non-limiting examples of active agents that are suitable for use with the subject meniscus implants include: cell growth media, such as Dulbecco's Modified Eagle Medium, fetal bovine serum, non-essential amino acids and antibiotics; growth and morphogenic factors such as fibroblast growth factor, transforming growth factors, vascular endothelial growth factor, epidermal growth factor, platelet derived growth factor, insulin-like growth factors), bone morphogenetic growth factors, bone morphogenetic-like proteins, transforming growth factors, nerve growth factors, and related proteins (growth factors are known in the art, see, e.g., Rosen & Thies, CELLULAR & MOLECULAR BASIS BONE FORMATION & REPAIR (R.G. Landes Co., Austin, Tex., 1995); anti-angiogenic proteins such as endostatin, and other naturally derived or genetically engineered proteins; polysaccharides, glycoproteins, or lipoproteins; anti-infectives such as antibiotics and antiviral agents, chemotherapeutic agents (i.e., anticancer agents), anti-rejection agents, analgesics and analgesic combinations, anti-inflammatory agents, steroids, or any combination thereof.

Methods for Repairing a Meniscal Defect:

Aspects of the invention include methods for repairing and/or replacing at least a portion of a meniscus in a subject. Any of the meniscus implants described herein can be implanted into a subject in need thereof in order to accomplish meniscus repair or regeneration. Accordingly, methods of repairing a meniscal defect or promoting meniscal regeneration in a subject are also provided herein. In one embodiment, a method comprises implanting a meniscus implant as described herein into a defect site in need of meniscus repair or regeneration.

The term "subject" includes, but is not limited to, humans, nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are included. In one embodiment, the subject is a mammal. In one embodiment, the subject is a human subject.

In some embodiments, a method can comprise securing a meniscus implant, or an anchor region thereof, at a defect site, and/or securing one or more anchor regions of a meniscus implant to at least one anatomical structure within a subject. In some embodiments, a method can further comprise removing at least a portion of a defective meniscus from the subject.

In some embodiments, a method can further comprise systemically and/or locally (e.g., to the meniscus implant site) administering to the subject at least one active agent described herein.

All patents and patent publications referred to herein are hereby incorporated by reference in their entirety.

Certain modifications and improvements will occur to those skilled in the art upon a reading of the foregoing description. It should be understood that not all such modifications and improvements have been included herein for the sake of conciseness and readability, but are properly within the scope of the following claims.

The invention claimed is:

1. A synthetic tissue structure comprising a plurality of layers deposited by a bioprinter, each layer comprising one or more synthetic tissue fibers comprising a solidified biocompatible matrix, wherein the type of matrix material varies in at least one direction within one or more synthetic tissue fibers in at least one layer, and wherein said tissue structure further comprises one or more anchor regions.

2. The synthetic tissue structure of claim 1, further comprising cells.

3. The synthetic tissue structure of claim 1, further comprising one or more active agents.

4. The synthetic tissue structure according to claim 1, wherein each of said layers comprises a matrix material that varies in type in at least one direction.

5. The synthetic tissue structure of claim 2, wherein at least one of said layers comprises a cell type and/or a cell density that varies in at least one direction within the one or more synthetic tissue fibers.

6. The synthetic tissue structure of claim 3, wherein at least one of said layers comprises one or more active agents that vary in type and/or amount in at least one direction within the one or more synthetic tissue fibers.

7. The synthetic tissue structure according to claim 1, wherein the periphery of said synthetic tissue structure comprises the one or more anchor regions, wherein the one or more anchor regions comprise one or more reinforced matrix materials.

8. The synthetic tissue structure of claim 1, wherein the matrix material comprises alginate, laminin, fibrin, hyaluronic acid, poly(ethylene) glycol based gel(s), gelatin, chitosan, agarose, or a combination thereof.

9. The synthetic tissue structure of claim 8, wherein the matrix material comprises alginate.

10. The synthetic tissue structure of claim 1, wherein the solidified biocompatible matrix is physiologically compatible.

11. The synthetic tissue structure of claim 10, wherein the solidified biocompatible matrix comprises one or more of collagen, fibronectin, thrombospondin, glycosaminoglycans (GAG), deoxyribonucleic acid (DNA), adhesion glycoproteins, elastin, and combinations thereof.

12. The synthetic tissue structure of claim 11, wherein the collagen is collagen I, collagen II, collagen III, collagen IV, collagen V, collagen VI, or collagen XVIII.

13. The synthetic tissue structure of claim 11, wherein the GAG is hyaluronic acid, chondroitin-6-sulfate, dermatan sulfate, chondroitin-4-sulfate, or keratin sulfate.

14. The synthetic tissue structure of claim 2, wherein the cells are mammalian cells; and wherein the mammalian cells are selected from the group consisting of fibroblasts, chondrocytes, fibrochondrocytes, primary human meniscus-derived chondrocytes, stem cells, bone marrow cells, embryonic stem cells, mesenchymal stem cells, bone marrow-derived mesenchymal stem cells, induced pluripotent stem cells, differentiated stem cells, tissue-derived cells, microvascular endothelial cells, and combinations thereof.

15. The synthetic tissue structure according to claim 1, wherein at least one of said layers comprises a single continuous synthetic tissue fiber dispensed from the bioprinter.

16. The synthetic tissue structure according to claim 15, wherein the single continuous synthetic tissue fiber dispensed from the bioprinter has a variable composition.

17. The synthetic tissue structure of claim 7, wherein the one or more anchor regions are comprised of polycaprolactone (PCL), poly(lactic-co-glycolic acid) (PLGA), polyurethane (PU), or any combination thereof, or one or more double network hydrogels.

18. The synthetic tissue structure of claim 7, wherein the one or more anchor regions further comprise a non-toxic dye.

19. The synthetic tissue structure according to claim 1, wherein the entire periphery of a layer of said synthetic tissue structure comprises a reinforced matrix material.

20. The synthetic tissue structure of claim 1, wherein the one or more anchor regions comprise one or more layers of higher strength material(s) deposited in alternation with one or more layers of softer matrix materials, wherein the softer matrix materials comprise materials conducive to cell survival and ingrowth.

21. The synthetic tissue structure of claim 20, wherein the one or more layers of higher strength materials are comprised of polycaprolactone (PCL), poly(lactic-co-glycolic acid) (PLGA), polyurethane (PU), or any combination thereof, or one or more double network hydrogels generated by combining at least two different hydrogel materials.

22. The synthetic tissue structure of claim 21, wherein the at least two different hydrogel materials include alginate, Gelatin methacryloyl (GelMA), methacryloyl polyethylene glycol (PEGMA), gellan gum, agarose, polyacrylamide, or any combination thereof.

23. The synthetic tissue structure of claim 1, wherein the one or more anchor regions comprise a non-toxic dye.

24. The synthetic tissue structure of claim 1, further comprising one or more reinforced peripheral regions.

25. The synthetic tissue structure of claim 7, further comprising one or more reinforced peripheral regions.

\* \* \* \* \*